United States Patent
Saitou et al.

(10) Patent No.: US 6,881,861 B2
(45) Date of Patent: Apr. 19, 2005

(54) METHOD OF PURIFYING GLUTAMIC ACID BY TRANSITION RECRYSTALLIZATION

(75) Inventors: Yoshiki Saitou, Kawasaki (JP); Takayuki Koda, Kawasaki (JP); Hiroshi Ueda, Kawasaki (JP); Kazuhiro Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/761,253

(22) Filed: Jan. 22, 2004

(65) Prior Publication Data

US 2004/0152917 A1 Aug. 5, 2004

Related U.S. Application Data

(63) Continuation of application No. PCT/JP02/06262, filed on Jun. 24, 2002.

(30) Foreign Application Priority Data

Jul. 30, 2001 (JP) ........................................ 2001-228882

(51) Int. Cl.[7] ...................... C07C 229/00; C07C 227/00
(52) U.S. Cl. ........................................ 562/573; 562/554
(58) Field of Search ................................. 562/573, 554

(56) References Cited

U.S. PATENT DOCUMENTS 3,565,950 A   2/1971   Ito et al. ..................... 260/527

FOREIGN PATENT DOCUMENTS

JP      45-4730      2/1970
JP      46-10844     3/1971

OTHER PUBLICATIONS

Int'l Search Report, Aug. 27, 2002, Japan Patent Office.
Int'l Preliminary Examination Report, Jun. 12, 2003, Japan Patent Office.

*Primary Examiner*—Cecilia J. Tsang
*Assistant Examiner*—Taylor Victor Oh
(74) *Attorney, Agent, or Firm*—Shelly Guest Cermak

(57) ABSTRACT

Disclosed herein is a method of purifying L-glutamic acid by transformation recrystallization which method comprises maintaining crude crystals of L-glutamic acid containing α crystals of L-glutamic acid in an aqueous solvent at a temperature of from 50° C. to the boiling point of said aqueous solvent in the coexistence of active carbon until about 30% or more of the crystals of L-glutamic acid have been transformed into β crystals thereof, the amount of said aqueous solvent being an amount not more than the amount sufficient (i.e., an amount insufficient) to form a saturated solution of said crystals of L-glutamic acid, according to which method purified crystals of L-glutamic acid can be obtained extremely rapidly and in high yields, and remarkably conveniently and easily on an industrial scale, as compared with the conventional transformation recrystallization method which is a hitherto common purification method of L-glutamic acid.

1 Claim, 1 Drawing Sheet

Effect of the amount of active carbon on the time required for transformation

Effect of the amount of active carbon on the conversion rate to PCA

METHOD OF PURIFYING GLUTAMIC ACID BY TRANSITION RECRYSTALLIZATION

This application is a continuation of application PCT/JP02/06262, filed Jun. 24, 2002.

TECHNICAL FIELD

The present invention relates to a method of purifying crude crystals of L-glutamic acid containing α crystals of L-glutamic acid by transition recrystallization (i.e., by recrystallization via transformation from the α-crystals of L-glutamic acid to the β-crystals thereof).

BACKGROUND ART

Currently, as is well known, crystals of L-glutamic acid are produced in Japan, United States of America, and other countries, in the form of crystals of the free acid, as they are, or its salts such as the sodium salt and the like, by a so-called fermentation process, for the purpose of using as seasonings, medicaments, foods, drinks, raw materials for synthetic fiber, and the like.

By the way, primary crystals of L-glutamic acid produced by a so-called fermentation process, i.e., crystals of L-glutamic acid obtained by culturing a microorganism having an ability of forming and accumulating L-glutamic acid, followed by separating the accumulated crystals from the fermentation broth, contain, in many cases, various impurities. Therefore, when the monosodium salt (crystal) of L-glutamic acid is to be produced by neutralizing such primary crystals as they are, the primary crystals may exert a large load on filtration, de-coloration, and crystallization of the monosodium salt of L-glutamic acid, in the production process of the monosodium salt of L-glutamic acid.

Because of this, as a method of purifying such crude crystals (primary crystals) of L-glutamic acid, there has been hitherto proposed a method of heating crude crystals of L-glutamic acid in an aqueous solvent to transform the α crystals (crystals having short rod shape or granular shape) into the β crystals (crystals having needle shape or scale-like shape), during which transformation course the impurities in the crude crystals of L-glutamic acid are released, and isolating the resulting purified crystals of L-glutamic acid from the mother liquor (Japanese Patent Publication Nos. 4730/1970 and 13806/1970, and so forth).

However, the following two problems arise in the transformation or transition recrystallization method. That is, (1) the transition may sometimes take a long period of time owing to the effects of the impurities. Additionally, (2) a long time heating may, in turn, sometimes induces the loss of L-glutamic acid owing to deterioration of L-glutamic acid (the formation of pyrrolidonecarboxylic acid (PCA) through dehydration reaction of L-glutamic acid).

DISCLOSURE OF THE INVENTION

Under the Background Art described above, it is an object of the present invention to produce purified crystals of L-glutamic acid for a short period of time and in high yields from crude crystals of L-glutamic acid containing α crystals of L-glutamic acid by improving the above-described transformation recrystallization method. In other words, an object of the present invention resides in the obtaining of purified crystals of L-glutamic acid extremely rapidly and in high yields, and remarkably conveniently and easily on an industrial scale, as compared with the transformation recrystallization method which is a hitherto common purification method of L-glutamic acid (the above Japanese Patent Publication Nos. 4730/1970 and 13806/1970).

As a result of intensive studies for achieving the above object, the present inventors have found that the transformation or transition can be accelerated by adding active carbon upon the transformation recrystallization, whereby β crystals of L-glutamic acid can be obtained in a short period of time in high yields. Based on these findings, they have accomplished the present invention.

Accordingly, the present invention relates to a method of purifying L-glutamic acid by transformation recrystallization which method comprises maintaining crude crystals of L-glutamic acid containing α crystals of L-glutamic acid in an aqueous solvent at a temperature of from 50° C. to the boiling point of said aqueous solvent in the coexistence of active carbon until about 30% or more of the crystals of L-glutamic acid have been transformed into β crystals thereof, the amount of said aqueous solvent being an amount not more than the amount sufficient (i.e., an amount insufficient) to form a saturated solution of said crystals of L-glutamic acid.

In the following will be described the present invention in detail.

Examples of the crude crystals of L-glutamic acid to which the purification method of the present invention is to be applied include crude crystals of L-glutamic acid containing α crystals of L-glutamic acid obtained by culturing a microorganism having an ability of forming and accumulating L-glutamic acid under a neutral pH condition to produce L-glutamic acid, followed by adding an acid to the fermentation broth to crystallize L-glutamic acid ("Amino Acid Fermentation", pp. 195–215, published 1986 by Gakkai Shuppan Center), crude crystals of L-glutamic acid obtained by culturing a microorganism having an ability of forming and accumulating L-glutamic acid under a low pH condition, followed by crystallizing the L-glutamic acid in the fermentation broth (Japanese Patent Application No. 241253/2000), and the like. Additionally, any of crude crystals of L-glutamic acid containing α crystals of L-glutamic acid may be the target of the purification method of the present invention, including not only such primary crystals but also crude crystals obtained in a subsequent process or crude crystals obtained by a process other than a fermentation process.

The whole or part of such crude crystals of L-glutamic acid is necessarily composed of α crystals thereof, but the content of α crystals is not particularly limited as far as the purification effect by the purification method of the present invention is achieved. Even in the case that most of the crystals are β crystals and only part of the crystals are α crystals (for example, the case that the content of α crystals is as small as 1% of the total glutamic acid), the purification effect can be achieved, like in the case that most crystals are α crystals.

In this connection, crude crystals of L-glutamic acid whose most crystals are α crystals are obtained, for example, in the case that α crystals are added as seed crystals, and crude crystals of L-glutamic acid whose most crystals are β crystals are obtained, for example, in the case that β crystals are added as seed crystals.

Examples of the aqueous solvent to be used in the method of the present invention include water, an aqueous solution of sodium glutamate, an aqueous solution of potassium glutamate, an aqueous solution of calcium glutamate, an aqueous solution of ammonium glutamate, and an aqueous solution of glutamic acid hydrochloride.

The amount thereof is an amount not more than the amount sufficient to form an aqueous saturated solution of the crude crystals to be purified. In other words, the amount is an amount capable of maintaining the crude crystals as a slurry. Moreover, the amount of the solvent is not particularly limited as far as the amount falls within the range. In general, when crude crystals containing a larger amount of impurities are to be treated, a lower concentration of slurry is preferred. However, when the purification is conducted in a dilute slurry state, the amount to be treated becomes larger and thus energy cost and the like are increased, so that it is not economical. On the other hand, the purification is conducted in an extremely high concentration state, structural viscosity sometimes occurs upon stirring, which may result in an increase of energy cost.

The active carbon to be used in the method of the present invention is not particularly limited, and a commercially available active carbon can be appropriately employed. As such active carbon, there may be mentioned "powdery active carbon SIW" (manufactured by Ajinomoto Fine-Techno Co., Inc.), and the like. With regard to the amount of active carbon to be employed, the aimed-at effect can be attained even in an amount of 0.1 wt % relative to the amount of crude crystals of L-glutamic acid to be purified, but, in general, a larger amount is preferably added when a slurry containing a larger amount of impurities is treated. However, from an economical viewpoint, the amount should be controlled, and an excessive addition is not necessary. For those who are of ordinary skill in the art, a suitable amount of active carbon can be very easily determined in a given case by conducting some preliminary experiment beforehand.

The temperature of the purification treatment (transformation or transition recrystallization temperature) is preferably a constant or varying temperature within the range of from 50° C. to the boiling point of the aqueous solvent to be used (more exactly, the boiling point of the liquid phase of the crude crystal-aqueous solvent mixed system). By leaving or stirring the mixed system under such temperature condition, the transformation or transition of α crystals of L-glutamic acid into β crystals thereof proceeds.

With regard to the transformation rate of α crystals of L-glutamic acid into β crystals thereof through which the aimed-at purification effect can be achieved, such purification effect may be attained when the transformation has proceeded even only a little, but it is preferred to leave or stir the mixed system at within the above temperature range until about 30% or more of the initial α crystals have been transformed into β crystals, like in the case described in the above Japanese Patent Publication No. 13806/1970.

Upon the separation of the purified L-glutamic acid crystals from the mother liquor after the transformation recrystallization operations have been completed, the active carbon does not necessarily need to be separated from such purified crystals of L-glutamic acid. For example, in the production method of the monosodium salt of L-glutamic acid by a fermentation process, the purified crystals of L-glutamic acid obtained by the transformation recrystallization are neutralized and dissolved with sodium hydroxide and then de-colored with active carbon ("Application Technology of Active Carbon,—Its Maintenance and Problems thereof—", pp. 441—441, published 2000 by Techno System). Therefore, in this case, the active carbon does not need to be separated from the purified crystals of L-glutamic acid after the transformation recrystallization step, and the active carbon may be properly separated after the de-coloration step. By the way, in the purification method of the present invention, the active carbon added to the slurry to be subjected to transformation recrystallization also exhibits de-coloring action even at this step. However, even when it is separated together with the purified crystals of glutamic acid, and then the purified glutamic acid is neutralized and dissolved by adding an sodium hydroxide aqueous solution, it does not desorb the once adsorbed impurities, so that de-coloration is conducted, without its separation, by adding new active carbon.

BEST MODE FOR CARRYING OUT THE INVENTION

In the following will be described the present invention more concretely with reference to the following examples, but it is not limited thereto.

EXAMPLE 1

Into a 200 ml three-neck flask fitted with a stirrer and a condenser tube was charged 30 g of crude α crystals of L-glutamic acid obtained by culturing a microorganism Enterobacter agglomerance (deposited under deposit No. FERM BP-7207, with an independent administrative institution, Sangyo Gijutsu Sogo Kenkyusho Tokkyo Seibutu Kitaku Center, Japan) having an ability of forming and accumulating L-glutamic acid under a low pH condition, followed by crystallizing the L-glutamic acid in the fermentation broth by adding α crystals of L-glutamic acid as seed crystals, 45 g of water, and 0 g, 0.3 g, or 3 g of "powdery active carbon SIW" (water content of 39 wt %) (manufactured by Ajinomoto Fine-Techno Co., Inc.). The mass within the flask was kept in temperature at 90° C. using an oil bath, whereby transformation recrystallization was carried out.

During the transformation recrystallization treatment, the slurry was sampled with the passage of time, and observed on an optical microscope to evaluate the transformation behavior. The time when the α crystals had not been observed was determined to be transformation completion time (time required for transformation).

Figure 1:
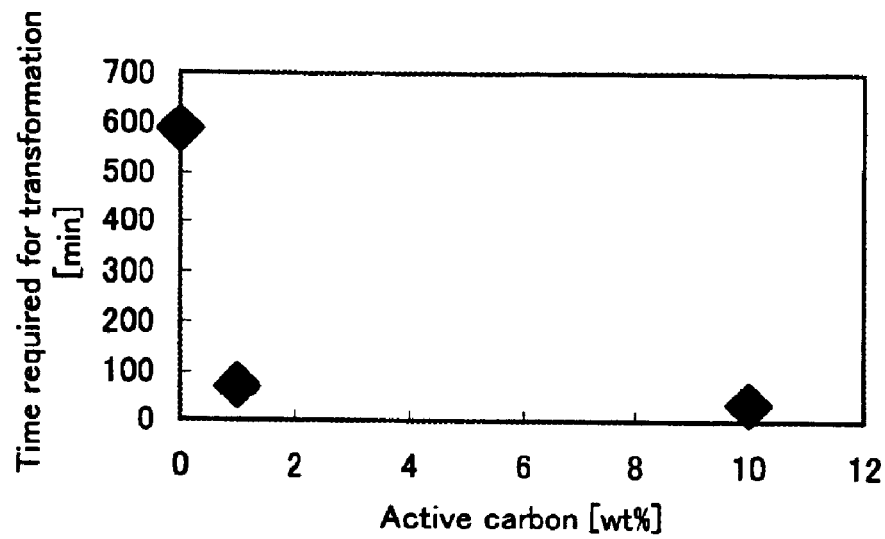
FIG. 1 shows the effect of the amount of active carbon on the time required for transformation (Example 1).

The results will be shown in FIG. 1. The transformation took 588 minutes in the case of no addition of active carbon, but the time was shortened to 70 minutes in the case of the coexistence of active carbon in an amount of 1 wt % relative to the L-glutamic acid and to 35 minutes in the case of the coexistence of active carbon in an amount of 10 wt %. Namely, the transformation was accelerated by the coexistence of active carbon, and, as a result, a large shortening of the transformation time succeeded.

Figure 2:
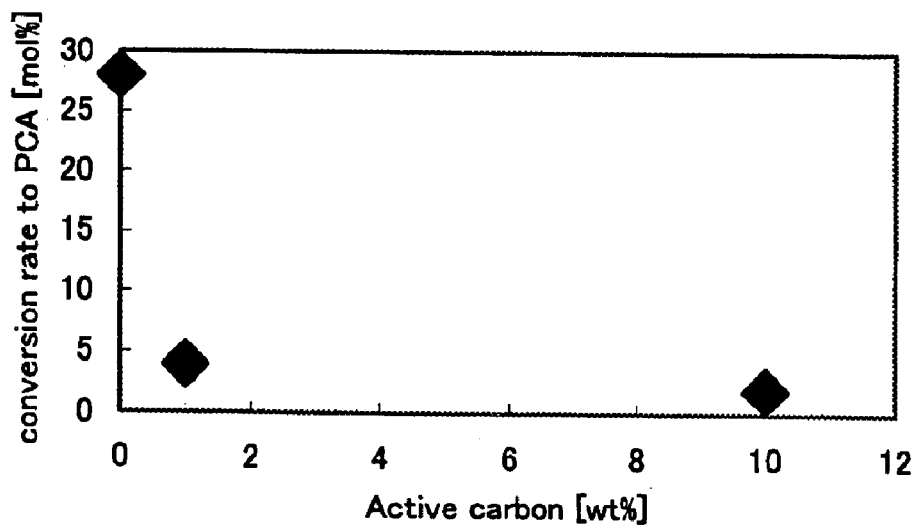
FIG. 2 shows the effect of the amount of active carbon on the conversion rate to PCA (Example 1).

Furthermore, the conversion rate of the L-glutamic acid into pyrrolidonecarboxylic acid through dehydration reaction, i.e., the loss rate of the L-glutamic acid was compared. The results will be shown in FIG. 2.

The conversion rate into pyrrolidonecarboxylic acid was 28 mol % in the case of no addition of active carbon, but it was 4 mol % in the case of the coexistence of active carbon in an amount of 1 wt % relative to the L-glutamic acid, and 2 mol % in the case of the coexistence of active carbon in an amount of 10 wt %. Namely, it can be understood that the loss of the L-glutamic acid caused by the conversion thereof into pyrrolidonecarboxilic acid could be largely eliminated by the coexistence of active carbon.

EXAMPLE 2

Into a 200 ml three-neck flask fitted with a stirrer and a condenser tube was charged 30 g of crude α crystals of L-glutamic acid obtained by culturing a microorganism Brevibacterium lactofermentum (deposited under deposit No. FERM BP-5189, with an independent administrative institution, Sangyo Gijutsu Sogo Kenkyusho Tokkyo Seibutu Kitaku Center, Japan) having an ability of forming and accumulating L-glutamic acid under a neutral pH condition, followed by crystallizing the L-glutamic acid in the fermentation broth by adding an acid, 45 g of water, and 0 g or 3 g of "powdery active carbon SIW" (water content of 39 wt %) (manufactured by Ajinomoto Fine-Techno Co., Inc.). The mass inside the flask was kept in temperature at 90° C. using an oil bath, whereby transformation recrystallization was carried out.

During the transformation recrystallization treatment, as in Example 1, the slurry was sampled with the passage of time, and observed on an optical microscope to evaluate the transformation behavior. The time when the α crystals had not been observed was determined to be transformation completion time.

The results have revealed that no transformation was observed at all even after 780 minutes in the case of no addition of active carbon, while all the original α crystals of L-glutamic acid were transformed into β crystals thereof in 175 minutes in the case of the coexistence of active carbon in an amount of 10 wt % relative to the L-glutamic acid. Namely, the transformation was accelerated by the coexistence of active carbon, and, as a result, a large shortening of the transformation time succeeded.

Furthermore, the conversion rate of the L-glutamic acid into pyrrolidonecarboxylic acid through dehydration reaction, i.e., the loss rate of the L-glutamic acid was compared.

The conversion rate into pyrrolidonecarboxylic acid was 35 mol % after 780 minutes in the case of no addition of active carbon, while it was 9 mol % after 175 minutes, i.e., transformation completion time, in the case of the coexistence of active carbon in an amount of 10 wt %. Namely, it can be understood that the loss of the L-glutamic acid caused by the conversion thereof into pyrrolidonecarboxilic acid could be largely eliminated by the coexistence of active carbon.

INDUSTRIAL APPLICABILITY

As is specifically shown in the above with reference to Examples, according to the transformation recrystallization method of the present invention in which method active carbon is caused to be coexistent, purified crystals of L-glutamic acid can be produced in a very short period of time and in high yields as compared with conventional methods, so that L-glutamic acid can be supplied to market in the form of inexpensive and highly pure crystals.

Each of the aforementioned documents, as well as the foreign priority document, Japan 2001-228882, filed Jul. 30, 2001, are hereby incorporated by reference.

What is claimed is:

1. A method of purifying L-glutamic acid by transformation recrystallization comprising maintaining crude crystals of L-glutamic acid containing α crystals of L-glutamic acid in an aqueous solvent as a slurry at a temperature of from 50° C. to the boiling point of said aqueous solvent in the presence of active carbon until about 30% or more of said crystals have been transformed into β crystals thereof the amount of said aqueous solvent being that which forms a saturated solution of said crystals of L-glutamic acid.

* * * * *